United States Patent
Durant et al.

(10) Patent No.: US 12,171,495 B2
(45) Date of Patent: Dec. 24, 2024

(54) LIGHT EXPOSURE QUANTIFICATION STRATEGY FOR PREVENTING LIGHT TOXICITY DURING AN OPHTHALMIC PROCEDURE

(71) Applicant: ALCON INC., Fribourg (CH)

(72) Inventors: Dan Durant, Rancho Santa Margarita, CA (US); Ashok Burton Tripathi, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 604 days.

(21) Appl. No.: 17/516,949

(22) Filed: Nov. 2, 2021

(65) Prior Publication Data

US 2022/0192489 A1    Jun. 23, 2022

Related U.S. Application Data

(60) Provisional application No. 63/129,139, filed on Dec. 22, 2020.

(51) Int. Cl.
*A61B 3/14*    (2006.01)
*G06T 7/00*    (2017.01)

(52) U.S. Cl.
CPC .............. *A61B 3/14* (2013.01); *G06T 7/0012* (2013.01); *G06T 2207/30041* (2013.01)

(58) Field of Classification Search
CPC ....... A61B 3/0008; A61B 3/14; A61B 3/0025; A61B 90/30; G06T 2207/30041; G06T 7/0012; A61F 2009/00863; A61F 2009/00874; A61F 9/007; A61F 9/0079; A61F 9/008

See application file for complete search history.

(56) References Cited

U.S. PATENT DOCUMENTS

| | | | |
|---|---|---|---|
| 7,499,624 B2 | 3/2009 | Dacquay et al. | |
| 7,837,373 B2 | 11/2010 | Chang | |
| 8,688,401 B2 | 4/2014 | Papac et al. | |
| 2010/0149073 A1* | 6/2010 | Chaum | G02B 27/0075 345/8 |
| 2016/0262605 A1 | 9/2016 | Taylor et al. | |
| 2018/0147087 A1 | 5/2018 | Bacher | |

FOREIGN PATENT DOCUMENTS

| | | |
|---|---|---|
| WO | 2019197993 A1 | 10/2019 |
| WO | 2020084611 A1 | 4/2020 |

* cited by examiner

*Primary Examiner* — Brandi N Thomas
(74) *Attorney, Agent, or Firm* — Quinn IP Law (57) ABSTRACT

A system and method quantify light exposure of a patient retina during an ophthalmic procedure. A light source illuminates the patient retina with directed light during the procedure to produce an illuminated retina surface. A camera collects image data of the illuminated retina surface. An electronic control unit (ECU) in communication with the camera and an indicator device receives the image data, calculates a cumulative energy spectral density of the directed light falling incident upon the retina, and executes a control action indicative of possible light toxicity in response to the cumulative energy spectral density exceeding a light toxicity threshold, including activating the indicator device. The illuminated retina surface may be divided into virtual zones, with the ECU mapping the cumulative energy spectral density to the illuminated retina surface. Each of the optional zones has a corresponding cumulative energy spectral density.

20 Claims, 3 Drawing Sheets

LIGHT EXPOSURE QUANTIFICATION STRATEGY FOR PREVENTING LIGHT TOXICITY DURING AN OPHTHALMIC PROCEDURE

CROSS-REFERENCE TO RELATED APPLICATIONS

This application claims priority to, and benefit of, U.S. Provisional Patent Application Ser. No. 63/129,139 (filed Dec. 22, 2020), which is hereby incorporated by reference in its entirety.

INTRODUCTION

The present disclosure relates to an automated strategy for quantifying exposure of a retina to light energy during an ophthalmic procedure. Certain ophthalmic surgical procedures require high magnification and imaging of the retina and surrounding tissue within the vitreous cavity of a patient's eye. During such procedures, the retina is illuminated by bright light, which is emitted primarily by a hand-operated light pipe/endoilluminator or another suitable directed light source. Vitrectomy is a representative procedure in which such directed light is used to illuminate the vitreous cavity. As understood in in the art, vitrectomy involves the precise removal of vitreous humor gel to facilitate access to and repair of a torn or separated retina, macular holes, or diseased/damaged ocular tissue. Cataract surgery and other ophthalmic procedures likewise use internally and/or externally directed light for the purpose of illumination and imaging.

The retina, which is a thin, highly delicate lining situated on posterior internal surfaces of the eyeball, acts as an appendage of the brain. That is, sensory neurons, intricate neural circuits, and synaptic connections of the retina respond to incident light with corresponding nerve impulses, which are ultimately transmitted to the brainstem via the optic nerve. Due to photosensitivity of the delicate retina tissue, directed light energy falling incident on the retina surface poses a risk of light toxicity, with this risk being highly variable and factor-dependent.

Currently, light output during ophthalmic procedures is characterized relative to a model using worst-case assumptions. Due to the wide variation between surgical lighting techniques of individual surgeons, differences in lighting technology, and the length of surgery, predictions made using worst-case models seldom coincide with actual light toxicity risk or exposure. As a result, a surgeon may be distracted during surgery by overaggressive light toxicity notifications and false alarms.

SUMMARY

Disclosed herein are automated light toxicity prevention methods and systems for accurately quantifying exposure of a patient retina to directed light energy during an ophthalmic procedure. The toxic potential of light energy during such a procedure widely varies based on a number of factors, including the linear distance between the retina and the light source, the exposed surface area of the retina, length of time that the area is exposed to light energy, and the spectral content and intensity of the light energy. By measuring working images of the retina during the procedure and quantifying light energy distribution in terms of cumulative energy spectral density, a more accurate assessment of true light energy exposure and attendant toxicity risk is afforded to the surgeon. This in turn allows the surgeon or any other attending clinician to make more informed decisions regarding retina illumination. Benefits of the present teachings include the potential use of higher intensity light and/or application of light of a different spectral content, perhaps for a longer duration before a light toxicity hazard warning manifests itself. Once a light toxicity hazard is indicated, an appropriate warning or notification is issued, along with possible adjustment of control settings of the light source in some embodiments.

In an exemplary embodiment, a system for quantifying light exposure of a patient retina during an ophthalmic procedure includes a light source, a camera, an indicator device, and an electronic control unit (ECU). The light source is configured to illuminate the patient retina with directed light during the ophthalmic procedure to thereby produce an illuminated retina surface. As this occurs, the camera collects digital or analog image data of the illuminated retina surface. The ECU, which is in communication with the camera, receives the image data and thereafter calculates a cumulative spectral energy density of the directed light energy falling incident upon the retina. The ECU then displays incident light energy information via the above-noted indicator device, itself having multiple possible configurations as described herein. In another embodiment, the ECU may be in communication with the light source, and may proceed to execute a control action relative to the light source based on assessment of possible light toxicity.

As used herein, the term "cumulative energy spectral density" refers to the energy density of incident light, integrated over time and spread across different wavelengths, i.e., the cumulative exposure of the retina to light energy in particular bandwidths of the electromagnetic spectrum, and to associated frequencies and intensities of such light. The control action is executed in response to the cumulative energy spectral density of delivered/incident light exceeding a light toxicity threshold, which may be a preset value determined by the user/surgeon or based on a calibration, and includes activating the indicator device.

The ECU as described herein integrates an energy level of the directed light over the course of the ophthalmic procedure, commencing with the onset of illumination of the retina. In other words, integration is not triggered when the light source is turned on, but rather when active illumination of the retina commences, i.e., when light energy falls incident upon the retina.

The ECU may optionally determine the above-noted cumulative energy spectral density as multiple different cumulative densities to provide a higher level of precision. For one example, the ECU may calculate cumulative light energy based on multiple light sources, such as a light pipe/probe and a chandelier. In another example, the ECU may calculate the cumulative density for multiple different areas or zones of the illuminated retina surface. In such an embodiment, the ECU is able to execute the control action in response to the cumulative energy spectral density of any one of the zones exceeding a light toxicity threshold, which itself may be several zone-specific thresholds to account for potential differences in light sensitivity across the exposed area of the retina.

The indicator device contemplated herein includes a display screen in certain embodiments. The ECU automatically presents a light energy distribution pattern or "heat map" of the illuminated retina surface to the surgeon via the display screen. The heat map is thus representative of the distribution of the cumulative energy spectral density, thereby pinpointing locations of relatively high or low energy concentrations, as delivered to the retina. A fundus image may be used as an optional backdrop to such a heat map, i.e., the heat map could be presented as an overlay or displayed on top of the fundus image to accurately indicate zones corresponding to local "hot spots", such as areas exposed to a disproportionately high amount of incident light energy. Optional approaches include altering overlay colors in a manner similar to adding yellow highlighter to parts of the displayed image that exceed a threshold.

In some aspects of the present disclosure, the ECU may be configured to automatically adjust control settings of the light source in response to exceeding the light toxicity threshold(s). For example, a wavelength and/or an intensity of the directed light may be modified as needed without manual intervention by the surgeon. The control action in such an embodiment may include automatically adjusting the wavelength and/or intensity in real-time via the ECU.

A method is also disclosed for quantifying light energy exposure of a patient retina during an ophthalmic procedure. An embodiment of the method includes illuminating the patient retina with directed light from a light source during the ophthalmic procedure to thereby produce an illuminated retina surface, and collecting image data of the illuminated retina surface using a camera. The method also includes receiving the image data from the camera via an ECU, and then calculating a cumulative energy spectral density, via the ECU, of the directed light energy falling incident upon the retina during the ophthalmic procedure. In response to the cumulative energy spectral density exceeding a light toxicity threshold, the method includes executing a control action via the ECU, wherein the control action is indicative of possible light toxicity, the control action including activating an indicator device.

The ECU in a possible embodiment includes a processor, input/output (I/O) circuitry in communication with the processor and with a light source, an indicator device, a camera, and memory. On the memory is recorded computer-readable instructions, the execution of which by the processor causes the ECU to receive collected image data from the camera during the ophthalmic procedure. The collected image data depicts the illuminated retina surface. Execution of the instructions also causes the ECU to calculate a cumulative energy spectral density of the directed light energy falling incident upon the retina during the ophthalmic procedure, and to execute a control action indicative of possible light toxicity in response to the cumulative energy spectral density exceeding a light toxicity threshold, including activating the indicator device. The threshold may be an arbitrary value set by the surgeon, based on experience with previous surgeries and the surgeon's medical judgement. Alternatively, the threshold may be based upon a calibration process which quantifies an appropriate safety threshold.

The above-described features and advantages and other possible features and advantages of the present disclosure will be apparent from the following detailed description of the best modes for carrying out the disclosure when taken in connection with the accompanying drawings.

The foregoing and other features of the present disclosure are more fully apparent from the following description and appended claims, taken in conjunction with the accompanying drawings.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Figure 1:
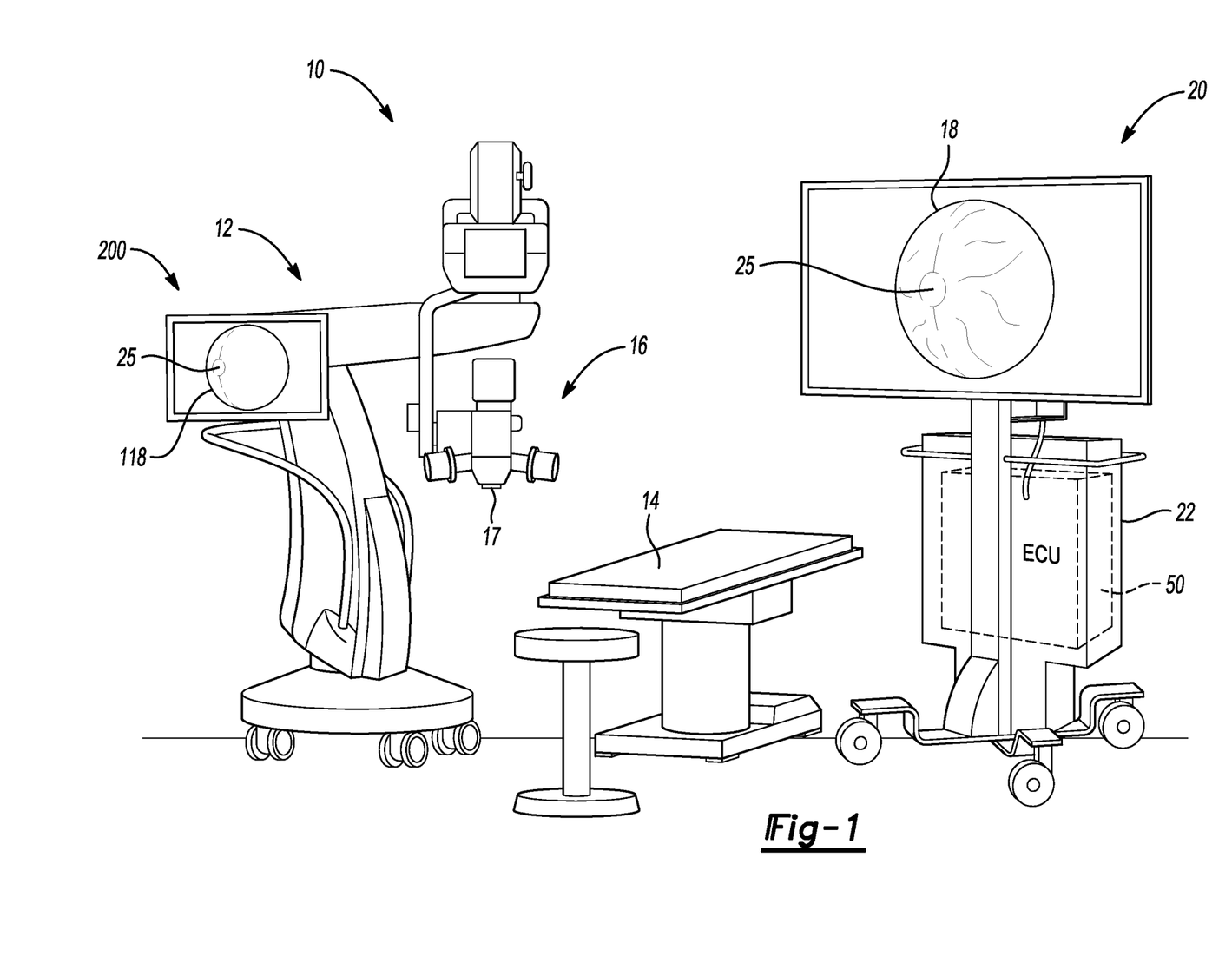
FIG. 1 is a schematic illustration of an operating room setup using an automated system for quantifying light exposure for preventing a possible light toxicity or exposure condition during a representative ophthalmic procedure.

Referring to the drawings, wherein like reference numbers refer to like components, a representative ophthalmic surgical suite 10 is depicted schematically in FIG. 1. As appreciated by those skilled in the art, such a surgical suite 10 may be equipped with a multi-axis surgical robot 12 and an operating table 14. When the surgical suite 10 is used for performing a representative vitreoretinal surgery or other surgical or diagnostic procedure, the surgical robot 12 is connected to an ophthalmic microscope 16 through which a surgeon (not shown) is able to view a patient's ocular anatomy under high magnification. Using associated hardware and software, the surgeon is able to view highly magnified images 18 and 118, e.g., of a retina 25 thereof, which may be achieved via corresponding high-resolution medical display screens 20 and 200.

Also present within the exemplary surgical suite 10 of FIG. 1 is a cabinet 22 containing an electronic control unit (ECU) 50, with an exemplary embodiment of the ECU 50 depicted in FIG. 2 and described in detail below. The cabinet 22, which is shown collocated with the display screen 20, may be positioned elsewhere in the suite 10 in other embodiments. Such a cabinet 22, which may be constructed of a lightweight and easily sanitized construction, e.g., painted aluminum or stainless steel, is used to house the ECU 50 and protect its constituent hardware from possible ingress of dust, debris, and moisture.

Within the scope of the disclosure, the vitreoretinal surgical procedure performed within the surgical suite 10 involves the use of directed task lighting for illumination of the retina 25. Such light is primarily emitted by a light source 32 as shown in FIG. 2, with additional lighting provided by an external lamp 17 mounted to the ophthalmic microscope 16. Over time, and based on a host of variable factors, the use of such light can pose a light toxicity risk affecting the photosensitivity functions of the retina 25. In order to mitigate such risk, the ECU 50 of the present disclosure is configured to automatically quantify light energy exposure of the retina 25, with an end goal of transmitting accurately derived alarms or warning to the attending surgeon. The ECU 50 may also perform optional exposure-reducing active control actions as set forth below.

Figure 2:
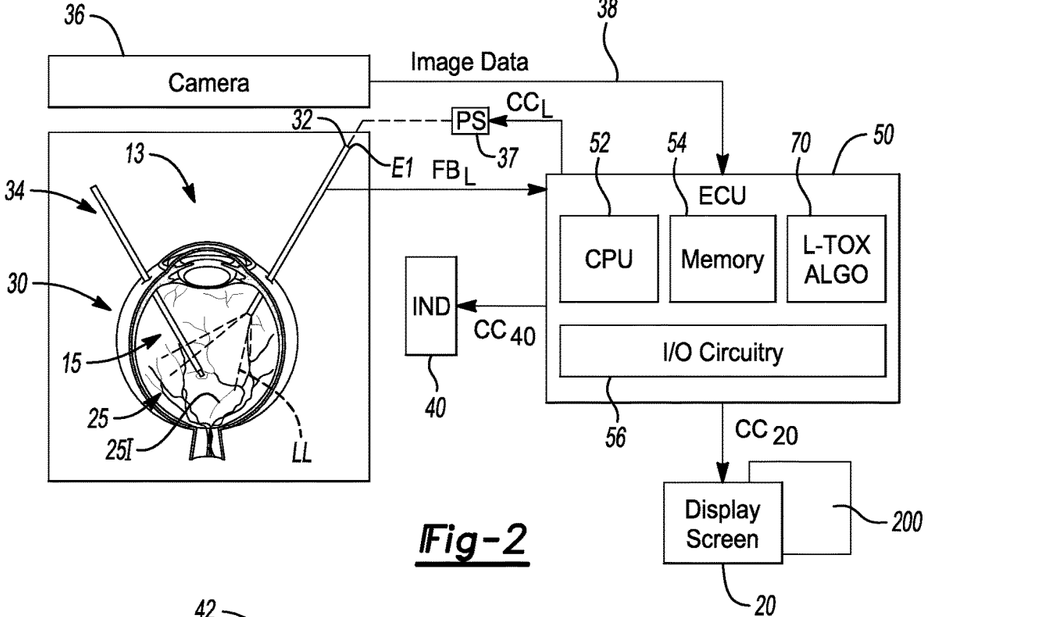
FIG. 2 is a schematic depiction of an embodiment of the automated system shown in FIG. 1.

Referring to FIG. 2, a representative patient eye 30 is shown undergoing an ophthalmic procedure 13, in this instance an invasive vitreoretinal surgery. During the course of an ophthalmic procedure 13 of this type, the light source 32 noted above is inserted into a vitreous cavity 15 of the patient eye 30. Light LL emitted from the light source 32, as well as some light from the microscope lamp 17 of FIG. 1, falls within a predetermined range of wavelengths depending on the illumination task. The light source 32 may be embodied as a light pipe or an endoilluminator in some embodiments, possibly with a controllable intensity and/or spectral content, i.e., the particular wavelengths and associated colors of light within the electromagnetic spectrum. Exemplary applications may be envisioned in which a surgeon desires a blue light shift for improved visibility, with the source light 32 possibly constructed to adjust its output spectrum in response to commands from the surgeon. Various lighting technologies may be used to emit the light LL, such as but not limited to red/green/blue (RGB) lasers, light-emitting diodes (LEDs), halogen bulbs, etc.

During the ophthalmic procedure 13, the surgeon may also insert a surgical tool 34 into the vitreous cavity 15 in order to perform a given operating task on or in proximity to the retina 25. Non-limiting exemplary embodiments of the surgical tool 34 include devices such as forceps, extrusion hand pieces, bladed vitrectomy probes, scissors, illuminated or non-illuminated laser probes, and/or infusion tools. With respect to the light source 32, the directed light LL is emitted from a distal end E1 thereof, where the directed light LL falls incident upon exposed surfaces of the retina 25 to produce an illuminated retina surface 25I. The light source 32 is coupled to an accompanying filtered power supply (PS) 37, such as a filtered wall outlet or a battery pack and power inverter suitable for ensuring reliable generation and transmission of the directed light (arrow LL).

Figure 4:
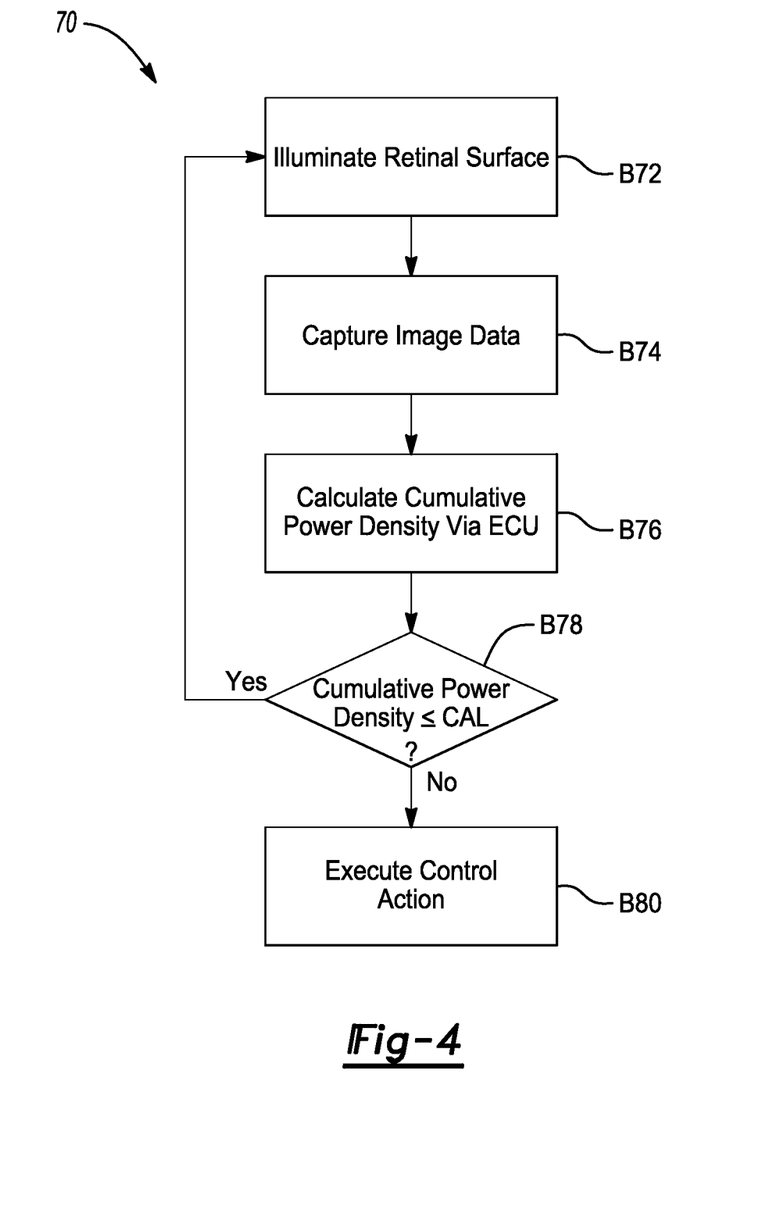
FIG. 4 is a flow chart describing an exemplary method for quantifying light energy exposure using the automated system shown in FIG. 1.

During the course of the ophthalmic procedure 13, a digital or analog camera 36 or another high-resolution medical imaging device collects image data 38 of the illuminated retina surface 25I, and thereafter transmits the collected image data 38 to the ECU 50 for processing in accordance with a light toxicity algorithm (L-TOX ALGO) 70. A method enabled by the algorithm 70 is depicted in FIG. 4 and described in detail below. An indicator device (IND) 40 is likewise in communication with the ECU 50, and is configured to activate/turn on in response to an indicator control signal (arrow $CC_{40}$) from the ECU 50. In response to the indicator control signal (arrow $CC_{40}$), and depending on the particular configuration of the indicator device 40, the indicator device 40 may provide a suitable audible, visible, and/or tactile alarm or warning.

For instance, the indicator device 40 may be embodied as a speaker, in which case the indicator control signal (arrow $CC_{40}$) may the indicator device 40 to sound an audible tone. Alternatively, the indicator device 40 may include a color-coded lamp, such that receipt of the indicator control signal (arrow $CC_{40}$) causes the indicator device 40 to light up in a readily identifiable manner, e.g., using red light. In either embodiment, the ECU 50 could also use the display screen 20 and/or 200 as part of the indicator device 40 to present an intuitive graphical depiction of light energy concentrations or distribution patterns on the illuminated retina surface 25I.

Within the scope of the present disclosure, the rate of light toxicity alarms is reduced relative to conventional approaches operating on a modeled worst-case scenario of the type described above. Instead, the ECU 50 in some embodiments is configured to receive light output data (arrow $F_{BL}$) as electronic feedback signals from the light source 32 that are indicative of the intensity, wavelength, temperature, and/or other relevant output parameters. The ECU 50 in such embodiments thereafter quantifies the actual distribution and energy spectral density of the directed light LL from the light source 32 across the illuminated retina surface 25I.

Still referring to FIG. 2, the ECU 50 is configured to receive the collected image data 38 from the camera 36 in real-time during the ophthalmic procedure 13, with the received collected image data 38 depicting the illuminated retina surface 25I and describing corresponding light intensity levels for each constituent image pixel. The ECU 50 estimates or calculates a cumulative energy spectral density of the directed light LL falling incident upon the retina 25 during the course of the ophthalmic procedure 13, with the ECU 50 doing so using the digital image data 38 and possibly the light output data (arrow $F_{BL}$) in different embodiments. As noted above, the term "cumulative energy spectral density" as used herein considers light energy density across different wavelengths of the electromagnetic spectrum, i.e., in particular wavelength ranges associated with light toxicity risk. The ECU 50 thereafter executes an appropriate control action indicative of possible light toxicity relative to one or more corresponding light toxicity thresholds.

Although the ECU 50 is depicted schematically as a unitary box for illustrative clarity and simplicity, the ECU 50 could include one or more networked devices each with a central processing unit (CPU) or other processor 52 and sufficient amounts of memory 54, including a non-transitory (e.g., tangible) medium that participates in providing data/instructions that may be read by the CPU 52. Instructions embodying the algorithm 70 may be stored in memory 54 and executed by the CPU 52 to perform the various functions described herein, thus enabling the present method. The memory 54 may take many forms, including but not limited to non-volatile media and volatile media.

As will be appreciated, non-volatile media may include optical and/or magnetic disks or other persistent memory, while volatile media may include dynamic random-access memory (DRAM), static RAM (SRAM), etc., any or all of which may constitute a main memory of the ECU 50. Input/output (I/O) circuitry 56 may be used to facilitate connection to and communication with the various peripheral devices used during the ophthalmic procedure 13, inclusive of the camera 36, the light source 32, the indicator device 40, and the display screen(s) 20 and/or 200. Other hardware not depicted but commonly used in the art may be included as part of the ECU 50, including but not limited to a local oscillator or high-speed clock, signal buffers, filters, etc.

Within the scope of the disclosure, the ECU 50 is programmed in software, equipped in hardware, and thus configured to integrate a power level over time of the directed light LL falling incident upon the retina 25 over the duration of the ophthalmic procedure 13. In this manner the ECU 50 derives the above-noted cumulative energy spectral density. That is, rather than considering the full duration over which the light source 32 is turned on, i.e., without respect to whether the directed light LL from the light source 32 actually illuminates any portion of the retina 25, the ECU 50 instead evaluates distribution and concentration of spectral energy from the distributed light LL on the retina 25 in more meaningful terms, e.g., in watts per minute, watts per hour, etc., possibly distinguishing between different zones of the retina 25.

Figure 3:
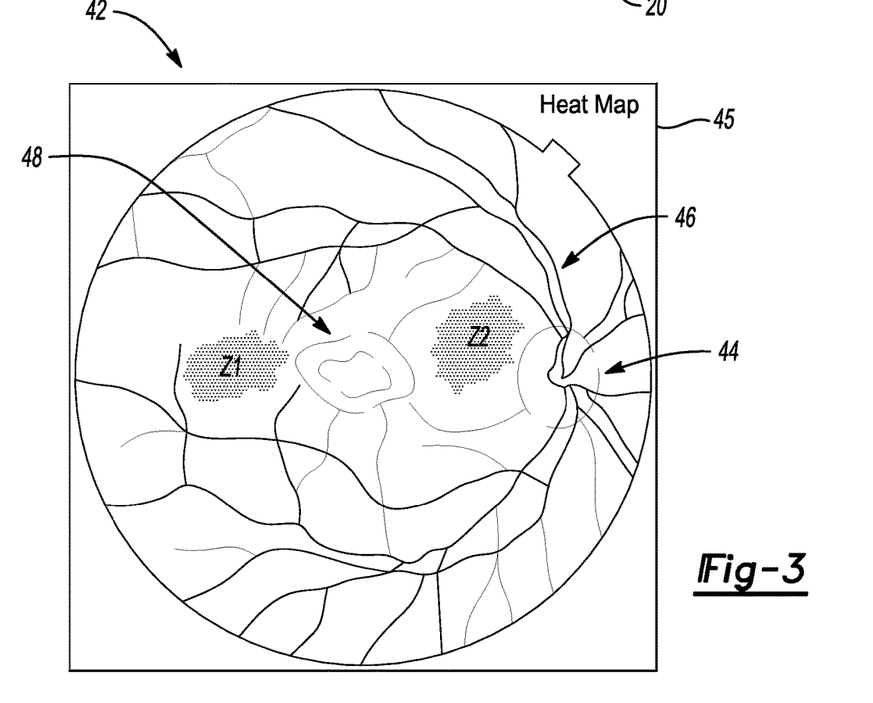
FIG. 3 is a schematic illustration of exemplary fundus image-based heat map in accordance with an aspect of the disclosure.

Referring briefly to FIG. 3, the retina 25 of FIG. 2 is shown as a representative fundus image 42. As appreciated in the art, a fundus image is a color, black and white, or grayscale image of various key structure of the retina 25, primarily the optic disc 44, the retinal artery 46 and surrounding veins stemming therefrom, and the macula 48. The fundus image 42, being ubiquitous in ophthalmic practice and thus familiar, may be used as a backdrop to a displayed heat map 45. In such a configuration, the ECU 50 may be configured to digitally divide or otherwise separate the illuminated retina surface 251 into multiple virtual zones, and to map the cumulative energy spectral density to the illuminated retina surface 251, such that each one of the multiple zones has a corresponding cumulative energy spectral density.

In such a configuration, the ECU 50 could optionally overlay the heat map 45 onto the fundus image 42 during the ophthalmic procedure 13 of FIG. 2, with this information presented in real-time via the display screen 20 and/or 200 of FIG. 1. The heat map 45 thus intuitively provides information that, at a glance, is indicative of a distribution or concentration of the cumulative energy spectral density across the illuminated retina surface 251 shown in FIG. 2. Such an approach provides a greater level of granularity or localized precision relative to treating the entire retina 25 as having equal light sensitivity, or as receiving equal exposure to the directed light LL of FIG. 2.

In the course of performing the representative ophthalmic procedure 13 of FIG. 2, a surgeon may be expected to move the distal end E1 around the vitreous cavity 15. As a result, the total exposed surface area of the retina 25 is likely to be illuminated unequally, and to a degree that is largely dependent on the location/distance and orientation of the distal end E1 relative to the retina 25, as well as on the intensity and other toxicity-relevant spectral content of the directed light LL. As a result, zones of the illuminated retina surface 251 of FIG. 2 may receive a greater density or concentration of the directed light LL relative to other zones, such as when the surgeon lingers in particular area of the retina 25 when performing an intricate surgical repair. From a qualitative standpoint, therefore, zones receiving a greater accumulated light energy density may be considered by the ECU 50 to be localized "hot spots". Two such zones are represented schematically in FIG. 3 as zones Z1 and Z2, with zones Z1 and Z2 depicted as flanking the macula 48 solely for the purposes of illustration.

The ECU 50 of the present disclosure is equipped to handle such disparity by integrating power both spatially, i.e., across the surface area of the retina 25, and temporally, i.e., with respect to the duration of exposure. The ECU 50 then executes a suitable control action in response to the cumulative energy spectral density of at least one of the multiple different zones Z1 and/or Z2, or of the entire illuminated retina surface 251, exceeding a corresponding light toxicity threshold. Such thresholds may be the same or zone-specific in different embodiments, as noted above, with the ECU 50 for instance using higher thresholds in zones in which tissue of the retina 25 is more resilient to light than others.

In still other embodiments, the total accumulated energy spectral density of the directed light LL falling incident on the retina 25 may be used, e.g., in watts per millimeter squared ($W/mm^2$), again possibly with different light toxicity thresholds applied to different zones of the retina 25 as noted above. For instance, zones in which photoreceptors of the retina 25 are more heavily concentrated than others may have a corresponding light toxicity threshold that is lower relative to other zones, with an effective "watts per rod" or "watts per cone" level of precision being realizable within the scope of the disclosure. Such light toxicity thresholds could be adjusted over time based on post-operative history or other factors to provide improved long-term results.

Referring now to FIG. 4, a method is made possible by execution of computer-readable instructions embodying the algorithm 70. That is, execution of instructions stored or recorded in memory (M) of the ECU 50 shown in FIG. 2 may cause the processor 52 and other hardware of the ECU 50 to perform the method. For clarity, therefore, such a method is referred to hereinafter as the method 70.

A representative embodiment of the method 70 commences with logic block B72, which includes illuminating the patient retina 25 of FIG. 2 with directed light LL from the light source 32, along with possibly some additional light from the microscope lamp 17 of FIG. 1, during the ophthalmic procedure 13, with the collective directed light LL producing the illuminated retina surface 251. Thus, surgical steps preceding implementation of logic block B72 may include creating an incision in the eye 30, inserting a canula (not shown), and inserting the light source 32 into the vitreous cavity 15. Once the distal end E1 of the light source 32 is present within the vitreous cavity 15 and energized by the power supply 37, the light source 32 in some embodiments initiates transmission of the light output data (arrow $FB_L$) to the ECU 50. Such light output data (arrow FBL) once again is primarily the contribution of the light source 32, but may also describe light emitted by the microscope lamp 17 in some embodiments. The method 70 then proceeds to logic block B74.

Logic block B74 of FIG. 4 may entail receiving the light output data (arrow $FB_L$) from the light source 32, the light output data being descriptive of an intensity and spectral content of directed light emitted by the light source when illuminating the patient retina. Logic block B74 also includes collecting the image data 38 of FIG. 2 using the camera 36, with the image data 38 possibly including two-dimensional or three-dimensional images of the illuminated retina surface 251. The camera 36 may be integral with the ophthalmic microscope 16 of FIG. 1 in some embodiments, or the camera 36 may be a separate device. As the collected image data 38 is formed in digital embodiments from image pixels, logic block B74 may include accompanying quantitative information describing corresponding illumination levels of each of the constituent image pixels, including for instance the intensity thereof.

As part of logic block B74, the image data 38 is transmitted to the ECU 50 over suitable transfer conductors (not shown). Logic block B74 thus also includes receiving the collected image data 38 from the camera 36 via the ECU 50. In conjunction with the light output data (arrow $FB_L$) provided in logic block B72, the image data 38 enables the ECU 50 to estimate power, intensity, wavelengths and other relevant energy spectral content of the directed light (LL) from the light source 32, as well as the distribution thereof across the retina 25. The method 70 then proceeds to logic block B76.

At logic block B76, the ECU 50 next estimates or calculates the cumulative energy spectral density of the directed light LL falling incident on the retina 25, using the light output data (arrow $FB_L$) of logic block B72 and the image data 38 of logic block B74. Estimation may occur in embodiments that are based on the collected image data 38 alone, e.g., using models based on the brightness, color, distribution, and other factors present in the images comprising the collected image data 38. More accurate results may be enjoyed in embodiments using the light output data (arrow $FB_L$), e.g., with foreknowledge of the power of the light source 32, the spread function of the light source 32, the distance of the light source 32 from the retina 25, and the length of time the retinal tissue is exposed to the light LL.

Logic block B76 may include calculating an average or normalized energy spectral density across the entire illuminated retina surface 251, or the ECU 50 may calculate multiple discrete energy spectral densities in a zone-specific manner. When using the latter approach, e.g., as depicted in FIG. 3, the surgeon is made aware of any disparity in light energy concentrations across the surface of the retina 25. The method proceeds to logic block B78 once the ECU 50 has calculated the cumulative energy spectral density or zone-specific energy spectral densities.

At logic block B78, the ECU 50 of FIG. 2 next compares the cumulative energy spectral density or densities to respective light toxicity thresholds. The method 70 repeats logic block B72 when none of the light toxicity thresholds have been exceeded. The method 70 proceeds in the alternative to logic block B80 when the ECU 50 determines that one or more of the light toxicity thresholds have been exceeded.

Logic block B80 involves, in response to the cumulative energy spectral density exceeding a light toxicity threshold, executing a control action via the ECU 50. As noted above, the control action is indicative of possible light toxicity, and includes activating the indicator device 40. As part of logic block B80, the ECU 50 may consider the magnitude by which a given light toxicity threshold was exceeded in logic block B78 when determining which of many possible control actions the ECU 50 should execute in a given situation. That is, the control action could be commensurate with the magnitude of a difference between the exceeded light toxicity threshold and the cumulative energy spectral density, with the ECU 50 possibly escalating the corresponding alarms as the magnitude increases.

An illustrative example includes establishing a threshold light toxicity level for representative zones Z1 and Z2 of FIG. 3. Through the course of the ophthalmic procedure 13, the ECU 50 automatically integrates power of the directed light LL, delivered over time, in different regions or zones of the illuminated retina surface 251, including the zones Z1 and Z2. The ECU 50 could display a color-coded version of the heat map 45 of FIG. 3 via the display screens 20 and/or 200 of FIG. 1, which would enable the surgeon to discern at a glance whether particular zones are being over-irradiated relative to others. In an embodiment, the ECU 50 could modify the color of "hotter" zones as cumulative energy spectral density in that zone increases, such as by gradually coloring the zone from yellow to red. Upon crossing a given light toxicity threshold for a given zone, the ECU 50 could activate the indicator device 40 of FIG. 2, e.g., a lamp or an audible alarm tone.

Additionally, the ECU 50 within the scope of the disclosure could respond to a given threshold light toxicity level being exceeded by automatically adjusting a setting of the light source 32. Such an option could be selectable by the surgeon or selectively bypassed or overridden in other embodiments. Representative control actions in such an event may include adjusting a power level from the power supply 37 of FIG. 2 to turn down the power of the light source 32, and/or changing the wavelength and/or intensity of the directed light LL emitted by the light source 32 during the course of the ophthalmic procedure 13. The latter control action could encompass changing the spectral content thereof to reduce the ultraviolet/violet/blue light content, thereby making the energy safer for the eye, albeit at the potential expense of less detail.

By using the ECU 50 of FIGS. 1 and 2, the intuitive heat map 45 of FIG. 3, and the algorithm 70 shown in FIG. 4, a surgeon performing the ophthalmic procedure 13 shown in FIG. 2 is made aware, in a more realistic and localized manner, of the light toxicity risk attendant to directing the incident light LL from the described light source 32 onto the retina 25. Because light toxicity alarms are not triggered unless and until a given energy spectral density-specific threshold has been exceeded, the present approach should help reduce the number of false alarms relative to conventional worst-case modeling scenarios.

Moreover, reducing the rate of false alarms provides a surgeon with an increased confidence level. Alarms that do sound in the course of performing the ophthalmic procedure 13 are, in other words, very likely to be true alarms and, as a result, less likely to be silenced or disregarded without action. Embodiments may be standalone, i.e., the ECU 50 and its attendant logic may be used with an existing ophthalmic microscope 16, camera 36, and light source 32. Alternatively, any or all of the described hardware could be integrated, such that the programmed functions of the ECU 50 when executing method 70 of FIG. 4 are seamless.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A system for quantifying light exposure of a patient retina during an ophthalmic procedure, the system comprising:

a light source configured to illuminate the patient retina with directed light during the ophthalmic procedure to thereby produce an illuminated retina surface;

a camera configured to collect image data of the illuminated retina surface as collected image data;

an indicator device; and an electronic control unit (ECU) in communication with the indicator device and the camera, wherein the ECU is configured to:

receive the collected image data from the camera depicting the illuminated retina surface;

estimate a cumulative energy spectral density of the directed light falling incident upon the retina during the ophthalmic procedure using the collected image data; and execute a control action indicative of possible light toxicity in response to the cumulative energy spectral density exceeding a light toxicity threshold, including activating the indicator device.

2. The system of claim 1, wherein the ECU is in communication with the light source and is configured to receive light output data therefrom, the light output data being descriptive of an intensity and spectral content of the light illuminating the patient retina.

3. The system of claim 1, wherein the ECU is configured to divide the illuminated retina surface into multiple virtual zones, and to map the cumulative energy spectral density to the illuminated retina surface such that each one of the multiple virtual zones has a corresponding cumulative energy spectral density.

4. The system of claim 3, wherein the light toxicity threshold includes a plurality of zone-specific light toxicity thresholds, and wherein the ECU is configured to determine, from the cumulative energy spectral density, a respective cumulative energy spectral density for each of the multiple zones, and to thereafter execute the control action in response to the respective cumulative energy spectral density of one the multiple virtual zones exceeding a corresponding one of the zone-specific light toxicity thresholds.

5. The system of claim 1, wherein the indicator device includes a speaker, and wherein the control action includes sounding an audible alarm via the speaker.

6. The system of claim 1, wherein the indicator device includes a color-coded lamp, and wherein the control action includes illuminating the color-coded lamp.

7. The system of claim 1, wherein the indicator device includes a display screen, and wherein the control action includes displaying information via the display screen indicative of the cumulative energy spectral density.

8. The system of claim 7, wherein ECU is configured to display a heat map of the illuminated retina surface via the display screen, the heat map being indicative of a distribution of the cumulative energy spectral density across the illuminated retina surface.

9. The system of claim 8, wherein the digital image data includes a fundus image of the patient retina, and wherein the heat map is displayed on the fundus image, such that the fundus image forms a backdrop for the heat map.

10. The system of claim 1, wherein the ECU is configured to selectively adjust a control setting of the light source, and wherein the control action includes adjusting, as the control setting, a wavelength and/or an intensity level of the directed light in real-time during the ophthalmic procedure.

11. The system of claim 10, wherein the light source is a light pipe or an endoilluminator having a variable intensity and/or spectral content.

12. A method for quantifying light exposure of a patient retina during an ophthalmic procedure, the method comprising:

illuminating the patient retina with directed light from a light source during the ophthalmic procedure to thereby produce an illuminated retina surface;

collecting image data of the illuminated retina surface, as collected image data, using a camera;

receiving the collected image data from the camera via an electronic control unit (ECU);

estimating a cumulative energy spectral density, via the ECU, of the directed light falling incident upon the retina during the ophthalmic procedure; and in response to the cumulative energy spectral density exceeding a light toxicity threshold, executing a control action via the ECU, wherein the control action is indicative of possible light toxicity, the control action including activating an indicator device.

13. The method of claim 12, further comprising:

dividing the illuminated retina surface via the ECU into multiple virtual zones; and mapping the cumulative energy spectral density to the illuminated retina surface via the ECU, such that each one of the multiple zones has a corresponding cumulative energy spectral density.

14. The method of claim 13, wherein the light toxicity threshold includes a plurality of zone-specific light toxicity thresholds, the method further comprising:

executing the control action via the ECU in response to the respective cumulative energy spectral density of one the multiple virtual zones exceeding a corresponding one of the zone-specific light toxicity thresholds.

15. The method of claim 12, the method further comprising:

receiving light output data from the light source, via the ECU, the light output data being descriptive of an intensity and spectral content of directed light emitted by the light source when illuminating the patient retina, wherein estimating the cumulative energy spectral density includes using the intensity and spectral content from the light output data.

16. The method of claim 12, wherein the indicator device includes a speaker and a color-coded lamp, and wherein executing the control action includes sounding an audible alarm via the speaker and illuminating the color-coded lamp.

17. The method of claim 12, wherein the indicator device includes a display screen, and wherein the control action includes displaying a heat map via the display screen indicative of the cumulative energy spectral density, the heat map being indicative of a distribution of the cumulative energy spectral density across the illuminated retina surface.

18. The method of claim 12, wherein executing the control action includes selectively adjusting a control setting of the light source via the ECU, the control setting including a wavelength and/or an intensity level of the directed light.

19. An electronic control unit (ECU) for quantifying light exposure of a patient retina during an ophthalmic procedure, the ECU being in communication with a light source during the ophthalmic procedure to thereby produce an illuminated retina surface, the ECU comprising:

a processor;

input/output (I/O) circuitry in communication with the processor, the light source, an indicator device, and a camera; and memory on which is recorded computer-readable instructions, wherein execution of the computer-readable instructions by the processor causes the ECU to:

receive collected image data from the camera during the ophthalmic procedure, wherein the collected image data depicts an illuminated retina surface of the patient retina;

receive light output data from the light source, the light output data being descriptive of an intensity and spectral content of directed light emitted by the light source when illuminating the patient retina;

calculate a cumulative energy spectral density of the directed light from the light source providing the illuminated retina surface during the ophthalmic procedure; and execute a control action indicative of possible light toxicity in response to the cumulative energy spectral density exceeding a light toxicity threshold, including activating the indicator device.

20. The ECU of claim 19, wherein execution of the computer-readable instructions by the processor causes the ECU to:

divide the illuminated retina surface into multiple virtual zones; and map the cumulative energy spectral density to the illuminated retina surface such that each one of the multiple virtual zones has a corresponding cumulative energy spectral density, wherein the light toxicity threshold includes a plurality of zone-specific light toxicity thresholds, and wherein the ECU determines, as the cumulative energy spectral density, a respective cumulative energy spectral density for each of the multiple virtual zones, and thereafter executes the control action in response to the respective cumulative energy spectral density of one the multiple virtual zones exceeding a corresponding one of the zone-specific light toxicity thresholds.

* * * * *